(12) United States Patent
De Meyer et al.

(10) Patent No.: US 8,592,161 B2
(45) Date of Patent: Nov. 26, 2013

(54) MUTATIONAL PROFILES IN HIV-1 PROTEASE CORRELATED WITH PHENOTYPIC DRUG RESISTANCE

(75) Inventors: Sandra De Meyer, Beerse (BE); Hilde Azijn, Leuven (BE); Marie-Pierre T. M. M. G. De Bethune, Everberg (BE)

(73) Assignee: Janssen R&D Ireland, Little Island, Co. Cork (IE)

( * ) Notice: Subject to any disclaimer, the term of this patent is extended or adjusted under 35 U.S.C. 154(b) by 1427 days.

(21) Appl. No.: 11/613,584

(22) Filed: Dec. 20, 2006

(65) Prior Publication Data

US 2007/0269816 A1    Nov. 22, 2007

Related U.S. Application Data

(62) Division of application No. 10/519,035, filed as application No. PCT/EP03/50277 on Jun. 30, 2003, now Pat. No. 7,217,506.

(60) Provisional application No. 60/392,753, filed on Jul. 1, 2002.

(51) Int. Cl.
| | |
|---|---|
| C12Q 1/68 | (2006.01) |
| C12Q 1/70 | (2006.01) |
| C12N 15/00 | (2006.01) |
| C12N 15/09 | (2006.01) |
| C12N 15/49 | (2006.01) |

(52) U.S. Cl.
USPC ............ 435/6.13; 435/5; 435/6.1; 435/69.1

(58) Field of Classification Search
None
See application file for complete search history.

(56) References Cited

U.S. PATENT DOCUMENTS

| | | | |
|---|---|---|---|
| 327,742 | A | 10/1885 | Uren |
| 5,631,128 | A | 5/1997 | Kozal et al. |
| 5,650,268 | A | 7/1997 | Kozal et al. |
| 5,856,086 | A | 1/1999 | Kozal et al. |
| 6,221,578 | B1 | 4/2001 | de Bethune et al. |
| 6,528,251 | B2 | 3/2003 | de Bethune et al. |
| 7,058,616 | B1 | 6/2006 | Larder et al. |
| 7,292,944 | B2 | 11/2007 | Larder et al. |
| 7,473,524 | B2 | 1/2009 | Azijn et al. |
| 7,494,768 | B1 | 2/2009 | Hertogs et al. |
| 2003/0190603 | A1 | 10/2003 | Larder et al. |
| 2004/0033489 | A1 | 2/2004 | Larder et al. |
| 2004/0073378 | A1 | 4/2004 | Dehertogh et al. |
| 2005/0214744 | A1 | 9/2005 | Azijn et al. |
| 2005/0239053 | A1 | 10/2005 | Azijn et al. |
| 2008/0286754 | A1 | 11/2008 | Dehertogh et al. |
| 2009/0061420 | A1 | 3/2009 | Azijn et al. |
| 2009/0162867 | A1 | 6/2009 | Hertogs et al. |

FOREIGN PATENT DOCUMENTS

| | | |
|---|---|---|
| CA | 2029123 A1 | 5/1991 |
| EP | 0406985 A2 | 1/1991 |
| EP | 0422762 A2 | 4/1991 |
| EP | 0428000 A1 | 5/1991 |
| EP | 0518557 A2 | 12/1992 |
| EP | 0824148 A2 | 2/1998 |
| EP | 1605064 A1 | 12/2005 |
| JP | 2002-199890 A | 7/2002 |
| WO | WO-9608580 A1 | 3/1996 |
| WO | WO-9727319 A1 | 7/1997 |
| WO | WO-9727332 A1 | 7/1997 |
| WO | WO-9727480 A1 | 7/1997 |
| WO | WO-9961658 A1 | 12/1999 |
| WO | WO-9961666 A1 | 12/1999 |
| WO | WO-9967417 A2 | 12/1999 |
| WO | WO-9967427 A1 | 12/1999 |
| WO | WO-9967428 A2 | 12/1999 |
| WO | WO-0073511 A1 | 12/2000 |
| WO | WO-0078994 A1 | 12/2000 |
| WO | WO-0078996 A1 | 12/2000 |
| WO | WO-0179540 A2 | 10/2001 |
| WO | WO-0181624 A1 | 11/2001 |
| WO | WO-0195230 A2 | 12/2001 |
| WO | WO-0222076 A2 | 3/2002 |
| WO | WO-0233402 A2 | 4/2002 |
| WO | WO-0238792 A2 | 5/2002 |
| WO | WO-02083657 A2 | 10/2002 |
| WO | WO 2004/003817 | 1/2004 |
| WO | WO-2004022523 A2 | 3/2004 |

OTHER PUBLICATIONS

Craig et al. HIV protease genotype and viral sensitivity to HIV protease inhibitors following saquinavir therapy. AIDS 1998, vol. 12, pp. 1611-1618.*

Robinson et al. HIV Type 1 Protease Cleavage Site Mutations and Viral Fitness: Implications for Drug Susceptibility Phenotyping Assays. Aids Research and Human Retroviruses 2000, vol. 16, No. 12, pp. 1149-1156.*

In the U.S. Appl. No. 09/580,491 Advisory Action dated Mar. 7, 2006, 2 pages.

(Continued)

*Primary Examiner* — Louise Humphrey

(74) *Attorney, Agent, or Firm* — Woodcock Washburn LLP

(57) ABSTRACT

The present invention is directed to the field of nucleic acid diagnostics and the identification of base variation in target nucleic acid sequences. More particularly, the present invention relates to the use of such genotypic characterization of a target population of HIV and the subsequent association, i.e., correlation, of this information to phenotypic interpretation in order to correlate virus mutational profiles with drug resistance. The invention also relates to methods of utilizing the mutational profiles of the invention in drug development, i.e., drug discovery, drug design, drug modification, and therapy, treatment design, clinical management and diagnostic analysis.

5 Claims, No Drawings

(56) References Cited

OTHER PUBLICATIONS

In the U.S. Appl. No. 09/580,491 Final Office Action dated Aug. 26, 2003, 8 pages.
In the U.S. Appl. No. 09/580,491 Final Office Action dated Jan. 22, 2008, 7 pages.
In the U.S. Appl. No. 09/580,491 Final Office Action dated Sep. 12, 2005, 4 pages.
In the U.S. Appl. No. 09/580,491 Non-Final Office Action dated Dec. 16, 2004, 6 pages.
In the U.S. Appl. No. 09/580,491 Non-Final Office Action dated Dec. 23, 2002, 6 pages.
In the U.S. Appl. No. 09/580,491 Non-Final Office Action dated Dec. 4, 2001, 7 pages.
In the U.S. Appl. No. 09/580,491 Non-Final Office Action dated May 9, 2007, 5 pages.
In the U.S. Appl. No. 09/580,491 Non-Final Office Action dated Sep. 26, 2006, 3 pages.
In the U.S. Appl. No. 10/399,920 Final Office Action dated Aug. 4, 2006, 8 pages.
In the U.S. Appl. No. 10/399,920 Final Office Action dated May 2, 2007, 9 pages.
In the U.S. Appl. No. 10/399,920 Non-Final Office Action dated Aug. 25, 2005, 10 pages.
In the U.S. Appl. No. 10/518,525 Final Office Action dated Feb. 7, 2007, 6 pages.
In the U.S. Appl. No. 10/518,525 Final Office Action dated Oct. 18, 2007, 6 pages.
In the U.S. Appl. No. 10/518,525 Non-Final Office Action dated May 10, 2006, 8 pages.
In the U.S. Appl. No. 10/519,035 Non-Final Office Action dated Dec. 16, 2005, 8 pages.
In the U.S. Appl. No. 10/519,436 Final Office Action dated Mar. 4, 2009, 10 pages.
In the U.S. Appl. No. 10/519,436 Final Office Action dated Mar. 7, 2007, 10 pages.
In the U.S. Appl. No. 10/519,436 Final Office Action dated May 11, 2010, 9 pages.
In the U.S. Appl. No. 10/519,436 Final Office Action dated Oct. 18, 2007, 8 pages.
In the U.S. Appl. No. 10/519,436 Non-Final Office Action dated Jun. 30, 2008, 9 pages.
In the U.S. Appl. No. 10/519,436 Non-Final Office Action dated Mar. 13, 2006, 10 pages.
In the U.S. Appl. No. 10/519,436 Non-Final Office Action dated Sep. 17, 2009, 13 pages.
In the U.S. Appl. No. 11/933,747 Final Office Action dated Apr. 5, 2010, 8 pages.
In the U.S. Appl. No. 11/933,747 Non-Final Office Action dated Aug. 7, 2009, 7 pages.
In the U.S. Appl. No. 12/261,475 Non-Final Office Action dated May 4, 2010, 6 pages.
In the U.S. Appl. No. 12/261,475 Non-Final Office Action dated Oct. 18, 2010, 9 pages.
In the U.S. Appl. No. 12/352,626 Non-Final Office Action dated Jul. 23, 2010, 7 pages.
Abremski et al., "pol protein HIV-1," downloaded from <http://www.ncbi.nlm.nih.gov/protein/AAG03320> 2000: 1-2.
Angarano et al.; "Genotype and Phenotype Resistance: An Overview," *Journal of Biological Regulators and Homeostatic Agents*, 2000; 14:11-14.
Anton et al.; "Comparative Patterns of HIV-1 Genotypic and Phenotypic Resistance Profiles in Gut and Plasma," *3rd International Workshop on HIV Drug Resistance and Treatment Strategies*, 1999; Abstract 86, 4(1).
Bacheler et al.; "Genotypic Correlates of Phenotypic Resistance to Efavirenz in Virus Isolates from Patients Failing Nonnucleoside Reverse Transcriptase Inhibitor Therapy," *Journal of Virology*, 2001; 75(11):4999-5088.
Bacheler et al.; "Human Immunodeficiency Virus Type 1 Mutations Selected in Patients Failing Efavirenz Combination Therapy," *Antimicrobial Agents and Chemotherapy*, 2000; 44(9):2475-2484.
Bakhanashvili et al.; "Mutational studies of human immunodeficiency virus type 1 reverse transcriptase: the involvement of residues 183 and 184 in the fidelity of DNA synthesis," *FEBS Letters*, 1996; 391(3):257-262.
Bally, F. et al.; "Polymorphism of HIV Type 1 Gag p7/p1 and p1/p6 Cleavage Sites: Clinical Significance and Implications for Resistance to Protease Inhibitors," *AIDS Research and Human Retroviruses*, 2000; 16(13):1209-1213.
Balotta et al.; "Prevalence of Transmitted Nucleoside Analogue-Resistant HIV-1 Strains and Pre-Existing Mutations in *pol* Reverse Transcriptase and Protease Region: Outcome After Treatment in Recently Infected Individuals," *Antiviral Therapy*, 2000 5:7-14.
Been-Tiktak et al.; "In-Vitro Selection of HIV-1 Variants Resistant to Non-Nucleoside Reverse Transcriptase Inhibitors in Monocyte-Derived Macrophages," *Journal of Antimicrobial Chemotherapy*, 1997; 40:847-853.
Beerenwinkel et al.; "Diversity and Complexity of HIV-1 Drug Resistance: A Bioinformatics Approach to Predicting Phenotype from Genotype," *PNAS*, 2002; 99(2):8271-8276.
Bloor et al.; "Lamivudine-Resistant HIV-1 Clinical Isolates Lacking the Met184Val Mutation have Novel Polymorphisms in RT," *3rd International Workshop on HIV Drug Resistance and Treatment Strategies*, 1999; Abstract 25, 4(1).
Calvez, V.; "Resistance to Antiretroviral Drugs," *Antiviral Therapy*, 1998; 3(4):5-7.
Casado et al.; "Rate of Non-nucleoside Reverse Transcriptase Inhibitor Resistance Among Patients Failing a Nevirapine Plus Protease Inhibitor-Containing Regimen," *3rd International Workshop on HIV Drug Resistance and Treatment Strategies*, 1999; Abstract 114, 1(1).
Catucci et al.; "Development and Significance of the HIV-1 Reverse Transcriptase M184V Mutation During Combination Therapy with Lamivudine, Zidovudine, and Protease Inhibitors," *Journal of Acquired Immune Deficiency Syndromes*, 1999; 21:203-208.
Chen et al.; "Drug Resistance Mutations as Predictors of Phenotypic Zidovudine Resistance in HIV-1 infection," *AIDS*, 1997; 11(12):1528-1529.
Clevenbergh et al.; "Prevalence of Nonucleoside Reverse Transcriptase Inhibitor (NNRTI) Resistance-Associated Mutations and Polymorphisms in NNRTIi-Naïve HIV-Infected Patients," *HIV Clin Trials*, 2002; 3(1):36-44.
Clotet et al.; "Efficacy and safety of darunavir-ritonavir at week 48 in treatment-experienced patients with HIV-1 infection in POWER 1 and 2: a pooled subgroup analysis of data from two randomised trials," *Lancet*, 2007; 369:1169-1178.
Coakley et al.; "Phenotypic and Genotypic Resistance Patterns of HIV-1 Isolates Derived from Individuals Treated with Didanosine and Stavudine," *AIDS*, 2000; 14:F9-F15.
Condra et al.; "Genotypic or phenotypic susceptibility testing may not predict clinical responses to indinavir," *1st International Workshop HIV Drug Resistance and Treatment Strategies and Eradication*, 1997; Abstract 47: 48-49.
Condra, Jon H.; "Resisting Resistance: Maximizing the Durability of Antiretroviral Therapy," *Annals of Internal Medicine*, 1998; 128(11):951-955.
Condra, Jon. et al.; "Genetic Correlates of in Vivo Viral Resistance to Indinavir, a Human Immunodeficiency Virus Type 1 Protease Inhibitor," *Journal of Virology*, 1996, 70(12):8270-8276.
Craig et al.; "HIV Protease Genotype and Viral Sensitivity to HIV Protease Inhibitors Following Saquinavir Therapy," *AIDS*, 1998; 12:1611-1618.
D'Aquila, R.; "HIV-1 Chemotherapy and Drug Resistance," *Clinical and Diagnostic Virology*, 1995; 3:299-316.
De Bethune et al.; "Does Natural or Acquired Resistance to Reverse Transcriptase and Protease Inhibitors, Observed in HIV-1 Groups M (Subtypes A-H) and O, Differ from Subtype B," *3rd International Workshop on HIV Drug Resistance and Treatment Strategies*, 1999; Abstract 49, 4(1).
De Oliveira, T. et al.; "Variability at Human Immunodeficiency Virus Type 1 Subtype C Protease Cleavage Sites: an Indication of Viral Fitness?," *Journal of Virology*, 2003; 77(17): 9422-9430.

(56) References Cited

OTHER PUBLICATIONS

Deeks et al.; "Correlation of Baseline Phenotypic Drug Susceptibility with 16 Week Virologic Response in a Pilot Combination Therapy Study in HIV-infected Patients who Failed Indinavir Therapy," $2^{nd}$ Int'l Workshop on HIV Drug Resistance and Treatment Strategies, Lake Maggiore, Italy, 1998; Abstract 53.

Deeks et al.; "Novel Four-Drug Salvage Treatment Regimens After Failure of a Human Immunodeficiency Virus Type 1 Protease Inhibitor-Containing Regimen: Antiviral Activity and Correlation of Baseline Phenotypic Drug Susceptibility with Virologic Outcome," The Journal of Infectious Disease, 1999; 179:1375-1381.

Descamps et al.; "Line Probe Assay for Detection of Human Immunodeficiency Virus type 1 Mutations Conferring Resistance to Nucleoside Inhibitors of Reverse Transcriptase: Comparison with Sequence Analysis," Journal of Clinical Microbiology, 1998; 36(7):2143-2145.

Descamps et al.; "Susceptibility of Human Immunodeficiency Virus Type 1 Group O Isolates to Antiretroviral Agents: In Vitro Phenotypic and Genotypic Analyses," Journal of Virology, 1997; 8893-8898.

Eastman et al.; "Comparison of Selective Polymerase Chain Reaction Primers and Differential Probe Hybridization of Polymerase Chain Reaction Products for Determination of Relative Amounts of Codon 215 Mutant and Wild-type HIV-1 Population," Journal of Acquired Immune Deficiency Syndromes and Human Retrovirology, 1995; 9:263-273.

Eastman, P. Scott, et al.; "Nonisotopic Hybridization Assay for Determination of Relative Amounts of Genotypic Human Immunodeficiency Virus Type 1 Zidovudine Resistance," Journal of Clinical Microbiology, 1995; 33(10): 2777-2780.

Edelstein et al.; "Oligonucleotide Ligation Assay for Detecting Mutations in the Human Immunodeficiency Virus Type 1 pol Gene That are Associated with Resistance to Zidovudine, Didanosine, and Lamivudine," Journal of Clinical Microbiology, 1998; 569-572.

Eriksson, Bertil F.H. et al.; "Phosphorylation of 3'-Azido'2'3'-Dideoxyuridine and Preferential Inhibition of Human and Simian Immunodeficiency Virus Reverse Transcriptases by Its 5'-Triphosphate," Antimicrobial Agents and Chemotherapy, 1989; 33(10):1729-1734.

Eshleman et al.; "Analysis of Human Immunodeficiency Virus Type 1 Drug Resistance in Children Receiving Nucleoside Analogue Reverse-Transcriptase Inhibitors plus Nevirapine, Nelfinavir, or Ritonavir (Pediatric AIDS Clinical Trials Group 377)," Journal of Infectious Disease, 2001; 183:1732-1738.

Eshleman et al.; "HIV1 isolate 420111k042398 from USA pol protein (pol) gene," downloaded from <http://www.ncbi.nlm.nih.gov/nuccore/AF357746> 2002: 1-2.

Esté et al.; "HIV Phenotype & Genotype Data Highlights," $2^{nd}$ International Workshop on HIV Drug Resistance and Treatment Strategies, Lake Maggiore, Italy, 1998.

Fodor et al.; "DNA Sequencing: Massively Parallel Genomics," Science, 1997; 277:393-395.

Fodor, Stephen P.A. et al.; "Multiplexed Biochemical Assays With Biological Chips," Nature, 1993; 364:555-556.

Gianotti et al.; "Study on Mutations and Antiretroviral Therapy (SMART): Preliminary Results," Antiviral Therapy, 1999; 4(3):65-69.

Gianotti et al.; "The Rationale for a Study on HIV-1 Reverse Transcriptase Mutations and Outcome of Antiretroviral Therapy with Two Nucleoside Analogs," Journal of biological Regulators and Homeostatic Agents, 1999; 158-162.

Gingeras et al.; "Use of Self-Sustained Sequence Replication Amplification Reaction to Analyze and Detect Mutations in Zidovudine-Resistant Human Immunodeficiency Virus," The Journal of Infectious Diseases, 1991; 164:1066-1074.

Gonzales et al.; "pol polyprotein (HIV-1)," downloaded from <http://www.ncbi.nlm.nih.gov/protein/AAK35843 2001>: 1-3.

Gunthard et al.; "Human Immunodeficiency Virus Replication and Genotypic Resistance in Blood and Lymph Nodes After a Year of Potent Antiretroviral Therapy," Journal of Virology, 1998; 2422-2428.

Hammer et al.; "Relationship of Phenotypic and Genotypic Resistance Profiles to Virological Outcome in a Trial of Abacavir, Nelfinavir, Efavirenz and Adefovir Dipivoxil in Patients with Virological Failure Receiving Indinavir," $3^{rd}$ International Workshop on HIV Drug Resistance and Treatment Strategies, 1999; 4(1); Abstract 64.

Harada et al.; "Infection of HTLV-IIVLAV in HTLV-I-Carrying Cells MT-2 and MT-4 and Application in a Plaque Assay," Science, 1985; 229(4713):563-566.

Harrigan et al.; "Drug Resistance and Short Term Virological Response in Patients Prescribed Multidrug Rescue Therapy," $3^{rd}$ International Workshop on HIV Drug Resistance and Treatment Strategies, 1999; 4(1); Abstract 62.

Hertogs et al.; "A Blinded Comparative Analysis of Two Genotyping Service Laboratories: Full Sequence Analysis of HIV-1 Protease and Reverse Transcriptase," $3^{rd}$ International Workshop on HIV Drug Resistance and Treatment Strategies, 1999; 4(1); Abstract 87.

Hertogs et al.; "A Novel Human Immunodeficiency Virus Type 1 Reverse Transcriptase Mutational Pattern Confers Phenotypic Lamivudine Resistance in the Absence of Mutation 184V," Antimicrobial Agents and Chemotherapy, 2000; 44(3):568-573.

Hertogs et al.; "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs," Antimicrobial Agents and Chemotherapy, 1998; 42(2):269-276.

Hertogs et al.; "Common, Rare and New Genotypic and/or Phenotypic HIV-1 Resistance Profiles Observed in Routine Clinical Practice: A Survey of Over 5000 Isolates," $3^{rd}$ International Workshop on HIV Drug Resistance and Treatment Strategies, 1999; 4(1); Abstract 108.

Hertogs et al.; "Comprehensive HIV Drug Resistance Monitoring Using Rapid, High-Throughput Phenotypic and Genotypic Assays with Correlative Data Analysis," International Congress on Drug Therapy in HIV Infections, 1998; 12(4):S11 (OP3.4).

Hertogs et al.; "Performance characteristics of phenotypic drug resistance testing (Antivirogram) in monitoring of anti-HIV therapy," International Workshop on HIV Drug Resistance, Treatment Strategies and Eradication, 1997; St. Petersburg, Florida; Abstract 43.

Hertogs et al.; "Testing for HIV-1 Drug Resistance: New Developments and Clinical Implications," Recent Res. Dev. Antimicrob. Agents Chemother., 1999; 3(Pt. 1):83-104.

Hertogs et al.; "The RT-Antivirogramm™: a rapid and accurate method to determine phenotypic (multi)-drug resistance in plasma of patients treated with various HIV-1 RT inhibitors," $5^{th}$ International Workshop on HIV Drug Resistance, 1996; Whistler, Canada, Abstract 64.

Hirsch et al.; "Antiretroviral Drug Resistance Testing in Adults with HIV Infection," JAMA, 1998; 279(24):1984-1991.

Holodniy et al.; "Determination of Human Immunodeficiency Virus RNA in Plasma and Cellular Viral DNA Genotypic Zidovudine Resistance and Viral Load During Zidovudine-Didanosine Combination Therapy," Journal of Virology, 1995; 69(6):3510-3516.

Holodniy et al.; "Human Immunodeficiency Virus Reverse Transcriptase Codon 215 Mutations Diminish Virologic Response to Didanosine-Zidovudine Therapy in Subjects with Non-Syncytium-Inducing Phenotype," The Journal of Infectious Diseases, 1996; 174:854-857.

Hsu et al.; "Higher Fidelity of RNA-Dependent DNA Mispair Extension by M184V Drug-Resistant than Wild-type Reverse Transcriptase of Human Immunodeficiency Virus Type 1," Nucleic Acids Research, 1997; 25(22):4532-4536.

Ibanez et al.; "Human Immunodeficiency Virus Type 1 Population Bottleneck During Individual Therapy Causes a Genetic Drift in the Env Quasispecies," Journal of General Virology, 2000; 81:85-95.

International Search Report dated Apr. 12, 2008, for PCT/EP08/056356.

International Search Report dated Jan. 4, 2005 for PCT/EP03/050280.

International Search Report dated Jul. 17, 2003, for PCT/EP01/012338.

International Search Report dated Nov. 10, 2003 for PCT/EP03/50277.

(56) References Cited

OTHER PUBLICATIONS

International Search Reported dated Oct. 22, 2003 for PCT/EP03/50279.
Iversen et al.; "Multidrug-Resistant Human Immunodeficiency Virus Type 1 Strains Resulting from Combination Antiretroviral Therapy," *Journal of Virology*; 1996; 70(2):1086-1090.
Ives et al.; "Emergence of Resistant Variants of HIV in vitro During Monotherapy with the Proteinase Inhibitor Saquinavir," *Journal of Antimicrobial Chemotherapy*, 1997; 39:771-779.
Japour et al.; "Standardized Peripheral Blood Mononuclear Cell Culture Assay for Determination of Drug Susceptibilities of Clinical Human Immunodeficiency Virus Type 1 Isolates," *Antimicrobial Agents Chemotherapy*, 1993; 37(5):1095-1101.
Kaufmann, G. R. et al.; "Impact of HIV Type 1 protease, Reverse Transcriptase, Cleavage Site, and p6 Mutations on the Virological Response to Quadruple Therapy with Saquinavir, Ritonavir, and Two Nucleoside Analogs," *AiIDS Research and Human Retroviruses*, 2001; 17(6):487-497.
Kellam et al.; "Fifth Mutation in Human Immunodeficiency Virus Type 1 Reverse Transcriptase Contributes to the Development of High-Level Resistance to Zidovudine," *Proc. Natl. Acad. Sci. USA*; 1992; 89:1934-1938.
Kellam et al.; "Recombinant Virus Assay: A Rapid, Phenotypic Assay for Assessment of Drug Susceptibility of Human Immunodeficiency Virus Type 1 Isolates," *Antimicrobial Agents and Chemotherapy*, 1994; 38(1):23-30.
Kemp et al.; "A Novel Polymorphism at Codon 333 of Human Immunodeficiency Virus Type 1 Reverse Transcriptase Can Facilitate Dual Resistance to Zidovudine and L-2', 3'-Dideoxy-3'-Thiacytidine," *Journal of Virology*, 1998; 72:5093-5098.
Kemp et al.; "Analysis of 5000 HIV-1 Clinical Samples Reveals Complex Non-Nucleoside RT Inhibitor Resistance Patterns," *Antiviral Therapy*, 1999:4 (Suppl 1):20.
Kempf et al.; "Analysis of Virological Response to ABT-378/Ritonavir Therapy in Protease Inhibitor-Experienced Patients with Respect to Baseline Viral Phenotype and Genotype," $3^{rd}$ *International Workshop on HIV Drug Resistance and Treatment Strategies*, 1999; 4(1); Abstract 8.
Kim et al.; "Anti-HIV Type 1 Activity of 3'-Fluoro-3'-Deoxythymidine for Several Different Multidrug-Resistant Mutants," *Aids Research and Human Retroviruses*, 2001; 17(5):401-407.
Konig et al.; "Azidothymidine Triphosphate Is an Inhibitor of Both Human Immunodeficiency Virus Type 1 Reverse Transcriptase and DNA Polymerase Gamma," *Antimicrobial Agents and Chemotherapy*, 1989; 33(12):2109-2114.
Korber et al.; "Numbering Positions in HIV Relative to HXB2CG," *Numbering Positions in HIV*, 1998; (III)102-111.
Kuritzkes, Daniel R.; "HIV Resistance to Current Therapies," *Antiviral Therapy*, 1997; 2(3);61-67.
Kusumi et al.; "Human Immunodeficiency Virus Type 1 Envelope Gene Structure and Diversity In Vivo and Cocultivation In Vitro," *Journal of Virology*, 1992; 66(2):875-885.
Larder et al.; "A Complete Survey in Over 1,500 Clinical HIV-1 Isolates, of Phenotypic and Genotypic Protease Inhibitor Resistance Profiles (Including Gag Cleavage Site Sequences) and Their Relation to Therapy History," *International Congress on Drug Therapy in HIV Infections*, 1998; 12(4):S11 Abstract Poster, OP3.5.
Larder et al.; "A Family of Insertion Mutations Between Codons 67 and 70 of Human Immunodeficiency Virus Type 1 Reverse Transcriptase Confer Multinucleoside Analog Resistance," *Antimicrob. Agents Chemother.*, 1999; 43(8):1961-1967.
Larder et al.; "HIV with Reduced Sensitivity to Zidovudine (AZT) Isolated During Prolonged Therapy," *Reports*, 1989; 243:1731-1734.
Larder et al.; "Multi-nucleoside drug resistance is conferred by a family of insertion mutations in HIV-1 reverse transcriptase," *Interscience Conference on Antimicrobial Agents and Chemotherapies*, 1998; 38:28 (Abstract No. LB-4).
Larder et al.; "Multiple Mutations in HIV-1 Reverse Transcriptase Confer High-Level Resistance to Zidovudine (AZI)," *Science*, 1989; 246(4934):1155-1158.
Larder et al.; "Predicting HIV-1 Phenotypic Resistance from Genotype Using a Large Phenotype-Genotype Relational Database," $3^{rd}$ *International Workshop on HIV Drug Resistance and Treatment Strategies*, 1999; 4(1); Abstract 59.
Larder et al.; "Tipranavir Inhibits Broadly Protease Inhibitor-Resistant HIV-1 Clinical Samples," *AIDS*, 2000; 14:1943-1948.
Larder et al.; "Tipranavir is Active Against a Large Selection of Highly Protease Inhibitor-Resistance HIV-1 Clinical Samples," $3^{rd}$ *International Workshop on HIV Drug Resistance and Treatment Strategies*, 1999; 4(1); Abstract 5.
Larder et al.; "Zidovudine Resistance Predicted by Direct Detection of Mutations in DNA from HIV-Infected Lymphocytes," *AIDS*, 1991; 5:137-144.
Leigh-Brown et al.; "Associations Between Amino Acids in the Evolution of HIV Type 1 Protease Sequences Under Indinavir Therapy," *AIDS Research and Human Retroviruses*, 1999; 15(3):247-253.
Lennerstrand et al.; "Mechanism of Zidovudine and Stavudine Resistance for HIV-1 RT with Amino Acid Insertions Between Codons 68 and 70," $3^{rd}$ *International Workshop on HIV Drug Resistance and Treatment Strategies*, 1999; 4(1); Abstract 32.
Lennerstrand, J. et al.; "A Method for Combined Immunoaffinity Purification and Assay of HIV-1 Reverse Transcriptase Activity Useful for Crude Samples," *Analytical Biochemistry*, 1996; 235(2):141-152.
Leriche-Guerin et al.; "Correlation Between Antiretroviral Resistance Mutations, Biological Parameters, and Clinical Evolution in Zidovudine-Treated Patients Infected with Human Immunodeficiency Virus Type 1," *Eur. J. Clin. Microbiol. Infect. Dis.*, 1997; 16:660-668.
Lorenzi et al.; "Impact of Drug Resistance Mutations on Virologic Response to Salvage Therapy," *AIDS*, 1999; 13:F17-F21.
Margot et al.; "Genotypic and Phenotypic Analyses of HIV-1 in Antiretroviral-Experienced Patients Treated with Tenofovir DF," *AIDS*, 2002; 16:1227-1235.
Martinez et al.; "protease (HIV-1)," downloaded from <http://www.ncbi.nlm.nih.gov/protein/AAF29689> 2000.
Matayoshi et al.; "Novel Flurogenic Substrates for Assaying Retroviral Proteases by Resonance Energy Transfer," *Science*, 1990; 247:954-958.
Mellors et al.; "Mutations in HIV-1 Reverse Transcriptase and Protease Associated with Drug Resistance," *Mutations in RT and Protease*, 1995; III-93-III-105.
Miller et al.; "Correlates of Resistance to Individual Nucleoside Drugs in Patients Who Have Never Taken Them," $3^{rd}$ *International Workshop on HIV Drug Resistance and Treatment Strategies*, 1999; 4(1); Abstract 41.
Miller et al.; "Patterns of Resistance and Cross-Resistance to Human Immunodeficiency Virus Type 1 Reverse Transcriptase Inhibitors in Patients Treated with the Nonnucleoside Reverse Transcriptase Inhibitor Loviride," *Antimicrobial Agents and Chemotherapy*, 1998; 42(12):3123-3129.
Miller et al.; "Phenotypic Susceptibility to Adefovir Dipivoxil in Clinical Samples with Defined RT Genotypic Resistance Patterns," $3^{rd}$ *International Workshop on HIV Drug Resistance and Treatment Strategies*, 1999; 4(1); Abstract 40.
Miller et al.; "Prevalence of Baseline Drug Resistance Mutations in Primary HIV Infection Patients from the QUEST Study," $3^{rd}$ *International Workshop on HIV Drug Resistance and Treatment Strategies*, 1999; 4(1); Abstract 141.
Mohamed et al.; "The Sequential Occurrence of *pol* 215 and *pol* 41 Zidovudine Resistance Mutations is Associated in an Additive Fashion with Low CD4 Cell Counts and High Plasma and Cellular HIV Viral Load," *Antiviral Research*, 1998; 39:47-53.
Moyle, G.; "Current Knowledge of HIV-1 Reverse Transcriptase Mutations Selected During Nucleoside Analogue Therapy: The Potential to Use Resistance Data to Guide Clinical Decisions," *Journal of Antimicrobial Chemotherapy*, 1997; 40:765-777.
Moyle, G.; "Viral Resistance Patterns Selected by Antiretroviral Drugs and Their Potential to Guide Treatment Choice," *Exp. Opin. Invest. Drugs*, 1997; 6(8):943-964.

(56) References Cited

OTHER PUBLICATIONS

Nakano et al.; "Clonal Selection of HIV Type 1 Variants Associated with Resistance to Foscarnet in Vitro: Confirmation by Molecular Evolutionary Analysis," *Aids Research and Human Retroviruses*, 1997; 13(7):563-573.

Parikh et al.; "Mutations in Retroviral Genes Associated with Drug Resistance," *HIV Database Review*, 2000; 106-161.

Patick et al.; "Antiviral and Resistance Studies of AG1343, an orally Bioavailable Inhibitor of Human Immunodeficiency Virus Protease," *Antimicrobial Agents and Chemotherapy*; 1996; 40(2):292-297.

Paulous et al.; "A 1 Week, Single-Cycle Protease Inhibitor Resistance Assay," *International Workshop on HIV Drug Resistance, Treatment Strategies and Eradication Session 3*, 1997; Abstract 46.

Pauwels et al.; "A Comprehensive HIV Drug Resistance Monitoring Using Rapid, High-Throughput Phenotypic and Genotypic Assays with Correlative Data Analysis," $2^{nd}$ *Annual Workshop on HIV Drug Resistance and Treatment Strategies*, Lake Maggiore, Italy, 1998; Abstract 51.

Pauwels et al.; "Rapid and Automated Tetrazolium-based Colorimetric Assay for the Detection of Anti-HIV Compounds," *Journal of Virological Methods*, 1988; 20(4):309-321.

Perez-Olmeda et al.; "Usefulness of Genotypic Analysis of Resistance to Nucleoside Analogues in the Clinical Setting," *Eur. J. Clin. Microbrial Infect. Dis.*, 1999; 18:448-449.

Piketty et al., "Efficacy of a Five-Drug Combination Including Ritonavir, Saquinavir and Efavirenz in Patients Who Failed on a Conventional Triple-Drug Regimen: Phenotypic Resistance to Protease Inhibitors Predicts Outcome of Therapy," *AIDS*, 1999; 13:F71-F77.

Proudfoot et al., "Novel Non-nucleoside Inhibitors of Human Immunodeficiency Virus Type 1 (HIV-1) Reserve Transcriptase. 4.1 2-Substituted Dipyridodiazepinones as Potent Inhibitors of Both Wild-Type and Cysteine-181 HIV-1 Reverse Transcriptase Enzymes," *Journal of Medical Chemistry*, 1995; 38(24):4830-4838.

Ren et al.; "Crystal Structures of HIV-1 RT Inhibitor Complexes: 'Second Generation' NNRTIs, Efavirenz and S-1153 (AG1549), and NNRTI- and NRTI-resistant Mutant Forms," $3^{rd}$ *International Workshop on HIV Drug Resistance and Treatment Strategies*, 1999; 4(1); Abstract 20.

Richman et al.; "Detection of Mutations Associated with Zidovudine Resistance in Human Immunodeficiency Virus by use of the Polymerase Chain Reaction," *Journal of Infectious Diseases*, 1991; 164:1075-1081.

Richman et al.; "Nevirapine Resistance Mutations of Human Immunodeficiency Virus Type 1 Selected during Therapy," *Journal of Virology*, 1994; 68(3):1660-1666.

Robinson et al.; "HIV Type 1 Protease Cleavage Site Mutations and Viral Fitness: Implications for Drug Susceptibility Phenotyping Assays," *AIDS Research and Human Retroviruses*, 2000; 16(12):1149-1156.

Rusconi, Stefano et al.; "Susceptibility to PNU-140690 (Tipranavir) of Human: Immunodeficiency Virus Type 1 Isolates Derived from Patients with Multidrug Resistance to Other Protease Inhibitors," *Antimicrobial Agents and Chemotherapy*, 2000; 44(5):1328-1332.

Saag et al.; "A Short-Term Clinical Evaluation of L-697,661, a Non-Nucleoside Inhibitor of HIV-1 Reverse Transcriptase," *The New England Journal of Medicine*; 1993; 329:1065-1072.

Schapiro et al.; "Clinical Cross-Resistance Between the HIV-1 Protease Inhibitors Saquinavir and Indinavir and Correlations with Genotypic Mutations," *AIDS*, 1999; 13:359-365.

Schinazi et al., "Mutations in Retroviral Genes Associated with Drug Resistance: 2000-2001 Update," *International Antiviral News*, 2000; 8(5):65-91.

Schinazi et al.; "Mutations in Retroviral Genes Associated with Drug Resistance," *International Antiviral News*, 1997; 5:129-142.

Schmidt et al.; "HIV-1 isolate 992286 from Germany pol protein (pol) gene," downloaded from <http://www.ncbi.nlm.nih.gov/nucleotide/AF347471>, 2002: 1-2.

Schmidt et al.; "pol protein (HIV-1)," downloaded from <http://www.ncbi.nlm.nih.gov/protein/AAK32676>, 2002: 1-2.

Schmidt et al.; "Simple Algorithm Derived from a Geno-/Phenotypic Database to Predict HIV-1 Protease Inhibitor Resistance," *AIDS*, 2000; 14:1731-1738.

Schmit et al.; "Recent Advances in Antiretroviral Therapy and HIV Infection Monitoring"; *Intervirology*, 1997; 40:304-321.

Schmit et al.; "Resistance-related Mutations in the HIV-1 Protease Gene of Patients Treated in 1 Year with the Protease Inhibitor Ritonavir (ABT-538)," *AIDS*, 1996; 10:995-999.

Seki et al.; "Isolation and characterization of human immunodeficiency virus type-1 mutants resistant to the non-nucleotide reverse transcriptase inhibitor MKC-442," *Antiviral Chemistry & Chemotherapy*, 1995; 6(2):73-79.

Servais et al.; "Comparison of DNA Sequencing and a Line Probe Assay for Detection of Human Immunodeficiency Virus Type 1 Drug Resistance Mutations in Patients Failing Highly Active Antiretroviral Therapy," *Journal of Clinical Microbiology*, 2001; 39(2):454-459.

Servais et al.; "Genotypic Correlates of Resistance to HIV-1 Protease Inhibitors on Longitudinal Data: The Role of Secondary Mutations," *Antiviral Therapy*, 2002; 6:239-248.

Servais, J.A.; "V-1 Reverse Transcriptase (human immunodeficiency virus 1), Accession No. CAB86592," downloaded from http://www/ncbi.nlm.nih.gov/entrez/viewer.fcgi?db=protein&val=7529531, 2006.

Shafer et al.; "Highly Active Antiretroviral Therapy for the Treatment of Infection with Human Immunodeficiency Virus Type 1," *Biomedicine & Pharmacotherapy*, 1999; 53:73-86.

Shafer et al.; "HIV-1 isolate PCCPROT48 from USA, protease (pol) gene," downloaded from <http://www.ncbi.nlm.nih.gov/nucleotide/AF085133>, 2001.

Shafer et al.; "Human Immunodeficiency Virus Reverse Transcriptase and Protease Sequence Database," *Nucleic Acids Research*, 1999; 27(1):348-352.

Shafer et al.; "Human Immunodeficiency Virus Reverse Transcriptase and Protease Sequence Database," *Nucleic Acids Research*, 2000; 28(1):346-348.

Shafer et al.; "Online Comparison of HIV-1 Drug Resistance Algorithms Identifies Rates and Causes of Discordant Interpretations," *Antiviral Therapy*, 2001; 6(Supplement 1):101-102.

Stein et al.; "Sequence Analysis of Proviral HIV RT Amplified Directly by a Semi-Quantitative Technique from AZT Treated Patients," *Journal of Medical Virology*, 1994; 44:115-121.

Stuyver et al.; "Line Probe Assay for Rapid Detection of Drug-Selected Mutations in the Human Immunodeficiency Virus Type 1 Reverse Transcriptase Gene," *Antimicrobial Agents and Chemotherapy*, 1997; 41(2):284-291.

Tamalet et al.; "Multidrug Resistance Genotypes (Insertions in the β3-β4 Finger Subdomain and MDR Mutations) of HIV-1 Reverse Transcriptase from Extensively Treated Patients: Incidence and Association with Other Resistance Mutations," *Virology*, 2000; 270:310-316.

Toth et al.; "A simple, continuous flurometric assay for HIV protease," *Int. J. Peptide Protein Res*, 1990: 544-550.

Tyagi et al.; "Continuous Assay of the Hydrolytic Activity of Human Immunodeficiency Virus-1 Protease," *Analytical Biochemistry*; 1992: 143-148.

Tyagi et al.; "Multicolor molecular beacons for allele discrimination," *Nature Biotechnology*, 1998: 49-50.

Vandamme et al.; "Managing Resistance to Anti-HIV Drugs," *Drugs*, 1999; 337-361.

Vasudevachari, M.D. et al.; "Emergence of Protease Inhibitor Resistance Mutations in Human Immunodeficiency Virus Type 1 Isolates from Patients and Rapid Screening Procedure for Their Detection," *Antimicrobial Agents and Chemotherapy*, 1996; 40(11):2535-2541.

Vella, S.; "Advances in the Virology of HIV Infection and Implications for Clinical Management," *Aids Clinical Care*, 1998; 10(3):17-19.

Verbiest et al.; "An Epidemiological Prospective Survey Assessing the Prevalence of HIV-1 Drug Resistance in 230 HIV-1-Positive Antiretroviral-Naïve Patients from the USA," $3^{rd}$ *International Workshop on HIV Drug Resistance and Treatment Strategies*, 1999; 4(1); Abstract 122.

Vergne et al., "POL precursor (HIV-1)" downloaded from http://www.ncbi.nlm.nih.gov/protein/CAC03089, 2000: 1-2.

(56) References Cited

OTHER PUBLICATIONS

Vergne et al.; "Genetic Diversity of Protease and Reverse Transcriptase Sequences in Non-Subtype-B Human Immunodeficiency Virus Type 1 Strains: Evidence of Many Minor Drug Resistance Mutations in Treatment-Naïve Patents," *Journal of Clinical Microbiology*, 2000; 38(11):3919-3925.

Verheyen, J. et al.; "Compensatory mutations at the HIV cleavage sites p7/p1 and p1/p6-gag in therapy-naive and therapy-experienced patients," *Antiviral Therapy*, 2006; 11(7): 879-887.

Villahermosa et al.; "Evaluation of Mixtures of Wild-Type HIV-1 and HIV-1 with Resistance Point Mutations Against Reverse Transcriptase Inhibitors," *Antiviral Therapy*, 1998; 3:221-227.

Vingerhoets et al.; "The Accuracy and Reproducibility of High Throughput Genotypic and Phenotypic HIV-1 Resistance Testing Under EN45001 and CLIA Accreditation Labels," *3rd International Workshop on HIV Drug Resistance and Treatment Strategies*, 1999; 4(1); Abstract 77.

Walter et al.; "Rapid, Phenotypic HIV-1 Drug Sensitivity Assay for Protease and Reverse Transcriptase Inhibitors," *Journal of Clinical Virology*, 1999; 13:71-80.

Wang et al.; "Design and Synthesis of New Fluorogenic HIV Protease Substrates Based on Resonance Energy Transfer," *Tetrahedron Letters*, 1990: 6493-6496.

Watkins et al.; "Protease HIV1," downloaded from http://www.ncbi.nlm.nih.gov/protein/Q7ZCQ9, 2000.

Watkins et al.; "Selection of High-Level Resistance to Human Immunodeficiency Virus Type 1 Protease Inhibitors," *Antimicrobial Agents and Chemotherapy*, 2003; 47(2):759-769.

Weber et al.; "Molecular Mechanics Analysis of Drug-Resistant Mutants of HIV Protease," *Protein Engineering*, 1999; 12(6);469-474.

Wegner et al.; "High Frequency of Antiretroviral Drug Resistance in HIV-1 From Recently Infected Therapy-Naïve Individuals," *3rd International Workshop on HIV Drug Resistance and Treatment Strategies*, 1999; 4(1); Abstract 119.

Wegner et al.; "Prevalence of Genotypic and Phenotypic Resistance to Anti-Retroviral Drugs in a Cohort of Therapy-Naïve HIV-1 Infected US Military Personnel," *AIDS*, 2000; 14:1009-1015.

Wegner et al.; "The Potential Role of Resistance Testing and Therapeutic Drug Monitoring in the Optimization of Antiretroviral Drug Therapy," *3rd International Workshop on HIV Drug Resistance and Treatment Strategies*, 1999; 4(1); Abstract 112.

Winters et al.; "Human Immunodeficiency Virus Type 1 Reverse Transcriptase Genotype and Drug Susceptibility Changes in Infected Individuals Receiving Dideoxyinosine Monotherapy for 1 to 2 Years," *Antimicrobial Agents and Chemotherapy*, 1997; 41(4): 757-762.

Yahi et al.; "Mutation Patterns of the Reverse Transcriptase and Protease Genes in Human Immunodeficiency Virus Type 1-Infected Patients Undergoing Combination Therapy: Survey of 787 Sequences," *Journal of Clinical Microbiology*, 1999; 37(12): 4099-4106.

Yee et al.; "Prospects for Gene Therapy Using HIV-Based Vectors," *Somatic Cell and Molecular Genetics*, 2001; 26:(1-6):159-174.

Yin et al.; "Overcoming HIV drug resistance through rational drug design based on molecular, biochemical, and structural profiles of HIV resistance," *Cellular Molecular Life Sciences*, 2006, 63:1706-1724.

Zhang Y-M, et al.; "Drug Resistance during Indinavir Therapy Is Caused by Mutations in the Protease Gene and in Its Gag Substrate Cleavage Sites," *Journal of Virology*, 1997; 71(9): 6662-6670.

Zolopa et al.; "A Comparison of Phenotypic, Genotypic and Clinical/Treatment History Predictors of Virological Response to Saquinavir/Ritonavir Salvage Therapy in a Clinic-based Cohort," *3rd International Workshop on HIV Drug Resistance and Treatment Strategies*, 1999; 4(1); Abstract 68.

Zolopa et al.; "HIV-1 Genotypic Resistance Patterns Predict Response to Saquinavir-Ritonavir Therapy in Patients in Whom Previous Protease Inhibitor Therapy Had Failed," *Annals of Internal Medicine*, 1999; 131(11): 813-821.

Condra et al, "HIV-1 Protease", Database Swissprot, Jul. 1, 1997, Database accession No. 010176, XP002258549.

* cited by examiner

MUTATIONAL PROFILES IN HIV-1 PROTEASE CORRELATED WITH PHENOTYPIC DRUG RESISTANCE

CROSS REFERENCE TO RELATED APPLICATIONS

This application is a Divisional application of U.S. application Ser. No. 10/519,035 filed Dec. 22, 2004 now U.S. Pat. No. 7,217,506, which is the national stage of Application No. PCT/EP2003/050277, filed Jun. 30, 2003, which application claims priority from U.S. Application No. 60/392,753, filed Jul. 1, 2002, the complete disclosures of which are hereby incorporated herein by reference for all purposes.

The present invention is directed to the field of nucleic acid diagnostics and the identification of base variation in target nucleic acid sequences. The invention provides novel mutations or mutational profiles of HIV-1 protease gene correlated with a phenotype causing alterations in sensitivity to anti-HIV drugs. The present invention also relates to the use of genotypic characterization of a target population of HIV and the subsequent association, i.e. correlation, of this information to phenotypic interpretation in order to correlate virus mutational profiles with drug resistance. The invention further relates to methods of utilizing the mutational profiles of the invention in databases, drug development, i.e., drug design, and drug modification, therapy and treatment design and clinical management.

The development and standardization of plasma HIV-1 RNA quantification assays has led to the use of viral load measurements as a key therapy response monitoring tool. The goal of antiretroviral therapy is to reduce plasma viremia to below the limit of detection on a long-term basis. However, in a significant number of patients, maximal suppression of virus replication is not achieved and for those in whom this goal is reached, a significant number experience viral load rebound. Viral load data provide no information on the cause of the failure.

Therapy failure may be due to a number of factors, including insufficient antiviral activity of the regimen, individual variations in drug metabolism and pharmacodynamics, difficulties in adhering to dosing regimen, requirements for treatment interruption due to toxicity, and viral drug resistance. Moreover, drug resistance may develop in a patient treated with sub-optimal antiretroviral therapy or a patient may be infected with drug-resistant HIV-1. Although drug resistance may not be the primary reason for therapy failure, in many cases any situation which permits viral replication in the presence of an inhibitor sets the stage for selection of resistant variants.

Viral drug resistance can be defined as any change in the virus that improves replication in the presence of an inhibitor HIV-1 drug resistance was first described in 1989 and involved patients that had been treated with zidovudine monotherapy (Larder, B. A., et al., Science 243, 1731-1734 (1989)). Emergence of resistance is almost always being observed during the course of treatment of patients with single antiretroviral drugs. Similarly, in vitro passage of viral cultures through several rounds of replication in the presence of antiretroviral compounds leads to the selection of viruses whose replication cycle is no longer susceptible to the antiretroviral compounds used. Resistance development has also been observed with the introduction of dual nucleoside reverse transcriptase inhibitors (NRTI) combination therapy as well as during the administering of the more potent non-nucleoside reverse transcriptase inhibitors (NNRTIs), protease inhibitors (PIs) and combinations thereof. Individual antiretroviral agents differ in the rate at which resistance develops: selection for resistant variants may occur within weeks of treatment or resistance may emerge after a longer treatment period.

Extensive genetic analysis of resistant viral isolates generated through in vivo or in vitro selection has revealed that resistance is generally caused by mutations at some specific site(s) of the viral genome. The mutational patterns that have been observed and reported for HIV-1 and that are correlated with drug resistance are very diverse: some antiretroviral agents require only one single genetic change, while others require multiple mutations for resistance to appear. A summary of mutations in the HIV genome correlated with drug resistance has been compiled (See e.g. Schinazi, Int. Antiviral News. 6, 65 (2000)). Electronic listings with mutations are available at different web locations such as hiv-web.lanl.gov/content/index, www.hivb.stanford.edu, and www.hivresistanceweb.com.

A genetic mutation is normally written in reference to the wild type virus, i.e., K101N refers to replacement of a Lysine at codon 101 with a Asparagine (The Molecular Biology of the Cell, 1994, Garland Publishing, NY). However, the mutations of the invention do not depend on the wild-type example listed in order to be within the practice of the invention. For example, the mutation 101N, refers to an Asparagine at the 101 codon regardless of the whether there was a Lysine at 101 prior to mutation. Alternatively, it may be said that a particular amino acid occurs at a given position, wherein "position" is equivalent to "codon". Mutations can also be identified in nucleic acids such as RNA, DNA, mRNA.

The degree of susceptibility of a genetic variant to an antiretroviral compound is expressed herein relative to the wild-type virus (HIV IIIB/LAI reference sequence) as found, for example, in GenBank, the sequence of which is hereby incorporated by reference (K03455, gi 327742, M38432). An alteration in viral drug sensitivity is defined as a change in resistance or a change in susceptibility of a viral strain to said drug. Susceptibilities are generally expressed as ratios of $EC_{50}$ or $EC_{90}$ values (the $EC_{50}$ or $EC_{90}$ value being the drug concentration at which 50% or 90% respectively of the viral population is inhibited from replicating) of a viral strain under investigation compared to the wild type strain. Hence, the susceptibility of a viral strain can be expressed as a fold change in susceptibility, wherein the fold change is derived from the ratio of for instance the $EC_{50}$ values of a mutant viral strain compared to the wild type. In particular, the susceptibility of a viral strain or population may also be expressed as resistance of a viral strain, wherein the result is indicated as a fold increase in $EC_{50}$ as compared to wild type $EC_{50}$.

As antiretroviral drugs are administered for longer periods, mostly in combination with each other, and as new antiretrovirals are being developed and added to the present drugs, new resistance-correlated genetic variants are being identified. Of particular importance is that the combination of antiretroviral agents can influence resistance characteristics.

Once viral resistance has developed, salvage therapy options may be severely restricted due to cross-resistance within each drug class. This is as important for initial treatment as for when a therapy change is called for in order to minimize the emergence of resistance and improve the long-term prognosis of the patient. The choice of therapy regimen will be supported by knowledge of the resistance profile of the circulating virus population. Additionally, therapy combinations will have a greater chance of being effective if they include agents that have a demonstrated potential of suppressing a particular virus population.

A number of applications describe the occurrence of mutations in HIV and their correlation to the development of drug resistance (WO 00/73511; WO 02/33402; WO 02/22076; WO 00/78996). The instant invention adds to the art mutations in the protease gene and their correlation i.e. association to viral drug resistance.

DETAILED DESCRIPTION OF THE INVENTION

The knowledge that mutations at position 41 and 70 correlate with a fold change in resistance can be applied in certain useful methods. The present invention relates to methods for evaluating the effectiveness of a protease inhibitor, based on the presence of at least one mutation selected from 41S, 41T, 41I, 41K, 41G and 70E, in HIV protease. In particular, the present invention relates to methods for evaluating the effectiveness of a protease inhibitor, based on the presence of at least one mutation selected from 41T, 41I, 41K, 41G and 70E, in HIV protease. The presence of at least one of said mutations correlates to a fold change in susceptibility or resistance of an HIV viral strain towards at least one protease drug. The effectiveness of a protease inhibitor in the presence of at least one of said mutations may be determined using e.g. enzymatic, phenotypic and genotypic methods. The correlation between the mutational profiles in HIV protease and drug usage may be useful for clinical toxicological and forensic applications. A combined approach involving genotypic and phenotypic resistance testing to correlate mutations with resistance phenotypes may be used. More in particular, the present invention provides a correlation between at least one strain of HIV having at least one mutation in HIV protease selected from 41T and 70E and a fold change in resistance. In one aspect of the invention, the HIV protease mutations, 41T and 70E, are both present in a viral strain.

The effectiveness of a protease inhibitor as an antiviral therapy for a patient infected with at least one HIV strain comprising mutant protease may be determined using a method comprising: (i) collecting a sample from an HIV-infected patient; (ii) determining whether the sample comprises a HIV protease having at least one mutation selected from 41S, 41T, 41I, 41K, 41G, and 70E; and (iii) correlating the presence of said at least one mutation of step (ii) to a change in effectiveness of said protease inhibitor. In particular, the effectiveness of a protease inhibitor as an antiviral therapy for a patient infected with at least one HIV strain comprising mutant protease may be determined using a method comprising: (i) collecting a sample from an HIV-infected patient; (ii) determining whether the sample comprises a HIV protease having at least one mutation selected from 41T, 41I, 41K, 41 G, and 70E; and (iii) correlating the presence of said at least one mutation of step (ii) to a change in effectiveness of said protease inhibitor.

In general a change in effectiveness can be expressed as a fold change in resistance. The fold change may be determined using a cellular assay including a cytopathogenic assay or the Antivirogram® (WO 97/27480). Alternatively, the fold change in susceptibility may be derived from database analysis such as the VirtualPhenotype™ (WO 01/79540). A decrease in susceptibility vis-á-vis the wild type virus correlates to an increased viral drug resistance, and hence reduced effectiveness of said drug. To determine the viral drug susceptibility the activity of the mutant enzyme may be compared to the activity of a wild type enzyme. In phenotyping assays pseudotyped viruses may be used. The mutations present in HIV protease may be determined at the nucleic acid or amino acid level using sequencing or hybridization techniques. A report may be generated that shows the region of the patient virus that has been sequenced, including at least one mutation selected from 41S, 41T, 41I, 41K, 41G and 70E, in particular, including at least one mutation selected from 41T, 41I, 41K, 41G and 70E. The report may include antiretroviral drugs, drug(s) for which a known resistance-associated mutation has been identified and/or to what extent the observed mutations selected from at least 41S, 41T, 41I, 41K, 41G and 70E are indicative of resistance to said drugs. In particular, the report may include drug(s) for which a known resistance-associated mutation has been identified and/or to what extent the observed mutations selected from at least 41T, 41I, 41K, 41G and 70E are indicative of resistance to said drugs. HIV may be present in combinations of several strains This may result in the presence of multiple mutations at a particular amino acid, including partial mutations. Partial mutations include the combination of the wild amino acid and a mutant amino acid at a particular position. Examples thereof include partial mutations at position 41 in HIV protease, including 41R/S, 41S/R, 41R/K, 41G/R, in particular 41R/K, 41G/R. The sample to be evaluated can be a bodily fluid including blood, serum, plasma, saliva, urine, or a tissue including gut tissues.

The fact that particular data correlate, indicates that a causal relationship exits between the data. Hence, a particular result renders a particular conclusion more likely than other conclusions.

A drug effective against mutant HIV protease may be identified by a method, comprising: (i) providing a nucleic acid comprising HIV protease comprising at least one mutation chosen from 41S, 41T, 41I, 41K, 41G and 70E; (ii) determining a phenotypic response to said drug for said HIV recombinant virus; and (iii) identifying a drug effective against mutant HIV based on the phenotypic response of step (ii). In particular, a drug effective against mutant HIV protease may be identified by a method, comprising: (i) providing a nucleic acid comprising HIV protease comprising at least one mutation chosen from 41T, 41I, 41K, 41G and 70E; (ii) determining a phenotypic response to said drug for said HIV recombinant virus; and (iii) identifying a drug effective against mutant HIV based on the phenotypic response of step (ii). The nucleic acid comprising HIV of step (i) may be recombined into a proviral nucleic acid deleted for said sequence to generate a recombinant HIV virus.

Identifying a drug is defined as making a selection of drugs clinically available based on the effectiveness of said drug. In addition to the selection of clinically available drugs, identifying also relates to the selection of clinical drug candidates. The phenotypic response may be determined using cellular assays such as the Antivirogram®. An effective drug against mutant HIV comprising at least one mutation in protease selected from 41T and 70E, is defined as a drug having a phenotypic response expressed, as e.g. a fold change in susceptibility lower than a defined cut-off that may be determined for a drug.

An other useful method for identifying a drug effective against mutant HIV protease comprising,
 (i) providing a HIV protease comprising at least one mutation chosen from 41S, 41T, 41I, 41K, 41G and 70E;
 (ii) determining the activity of said drug on said HIV protease;
 (iii) determining the activity of said drug on wild type HIV protease;
 (iv) determining the ratio of the activity determined in step (iii) over the activity determined in step (ii);
 (v) identifying an effective drug against mutant HIV based on the ratio of step (iv).

In particular, a usefull method for identifying a drug effective against mutant HIV protease comprising:

(i) providing a HIV protease comprising at least one mutation chosen from 41T, 41I, 41K, 41G and 70E;
(ii) determining the activity of said drug on said HIV protease;
(iii) determining the activity of said drug on wild type HIV protease;
(iv) determining the ratio of the activity determined in step (iii) over the activity determined in step (ii);
(v) identifying an effective drug against mutant HIV based on the ratio of step (iv).

A ratio lower than a defined cut-off value that can be specific for said drug is indicative that the drug is effective against mutant HIV (WO 02/33402).

The activity of said drug on said HIV protease, having at least one mutation selected from 41S, 41T, 41I, 41K, 41G and 70E, in particular 41T, 41I, 41K, 41G and 70E, can be determined in an enzymatic assay, wherein the mutant protease, is compared to the wild type enzyme by its enzymatic characteristics (e.g. Maximal velocity ($V_{max}$), Michaelis-Menten constant ($K_m$), catalytic constant ($k_{cat}$)). A activity means any output generated by the assay including fluorescence, fluorescence polarization, luminiscence, absorbance, radioactivity, resonance energy transfer mechanisms, magnetism. The use of fluorescent substrates to measure the HIV protease activity was described by e.g. Matayoshi et al. [Science 1990, 247, 954], Tyagi et al. [Anal. Biochem. 1992, 200(1), 143], Toth et al. [Int. J. Pept. Protein Res. 1990, 36(6), 544] and Wang et al. [Tetrahedron 1990, 31(45), 6493] and in several patent applications [see e.g. WO99/67417; EP428000, EP518557]. A suitable substrate for the enzymatic determination is R-E(EDANS)—S-Q-N—Y—P—I—V-Q-K(DABCYL)-R—OH (Science, 1989, 247, 954-958). Alternatively HPLC based methods may be used to determine the activity.

The response of a mutant HIV protease having at least one mutation selected from 41S, 41T, 41I, 41K, 41G and 70E, in particular 41T, 41I, 41K, 41G and 70E, may be expressed as viral fitness (WO 00/78994). This viral fitness can be defined as hee ability of a viral strain to replicate in the presence or absence of a component, such as a protease inhibitor. This viral fitness is dependent on a combination of factors including viral factors which include mutations occurring in viral proteins, such as the mutations described herein, host factors which include immune responses, differential expression of membrane proteins and selective pressures which include the presence of antiviral agents such as protease inhibitors.

Interestingly, protease inhibitors that can be used in the present methods include Nelfinavir, Saquinavir, Indinavir, Amprenavir, Tipranavir, Lopinavir, Ritonavir, Palinavir, Atazanavir, Mozenavir, Fosamprenavir, compound 1 Carbamic acid, [(1S,2R)-3-[[(4-aminophenyl)sulfonyl](2-methylpropyl)amino]-2-hydroxy-1-(phenylmethyl)propyl]-, (3R,3aS,6aR)-hexahydrofuro[2,3-b]furan-3-yl ester, compound 1), and compound 2, which has been described as a HIV protease inhibitor in WO02/083657 and which can be prepared according to the procedures described therein. Compound 2 has the following chemical structure:

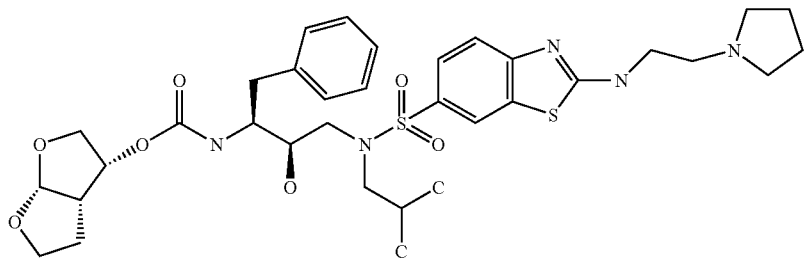 [SMILES: CC(C)CN(C[C@@H](O)[C@H](Cc1ccccc1)NC(=O)O[C@H]1CO[C@H]2OCC[C@H]21)S(=O)(=O)c1ccc2nc(NCCN3CCCC3)sc2c1]

In an embodiment, the protease inhibitor is selected from Indinavir, Saquinavir, Lopinavir, Nelfinavir, compound 1, and compound 2. In particular, the protease inhibitor is selected from Indinavir, Saquinavir, Lopinavir and compound 1.

Conveniently, the methods of the present invention are performed using samples of an HIV-infected patient that has been treated with at least a protease inhibitor. More in particular, the patient contains mutant viruses bearing at least one additional mutation at position in the HIV protease selected from 10, 30, 33, 46, 47, 50, 54, 63, 71, 74, 77, 82, 84, 88 or 90. Even more in particular, the mutant viruses are resistant towards the therapy the patient is taken.

A vector comprising an HIV sequence having at least one mutation in the HIV protease gene chosen from 41S, 41T, 41I, 41K, 41G and 70E may be useful for the phenotypic analysis. In particular, a vector comprising an HIV sequence having at least one mutation in the HIV protease gene chosen from 41T, 41I, 4K, 41G and 70E may be useful for the phenotypic analysis. The present knowledge about the correlation between a fold change in susceptibility and the presence of at least one mutation selected from 41S, 41T, 41I, 41K, 41G and 70E in HIV protease can be used to prepare an isolated and purified HIV protease sequence having at least one mutation selected from 41S, 41T, 41I, 41K, 41G and 70E. In particular, the knowledge about the correlation between a fold change in susceptibility and the presence of at least one mutation selected from 41T, 41I, 41K, 41G and 70E in HIV protease can be used to prepare an isolated and purified HIV protease sequence having at least one mutation selected from 41T, 41I, 41K, 41G and 70E.

The knowledge of the mutations of the present invention offers the possibility to develop probes and primers directed to said mutations. An isolated and purified oligonucleotide comprising a HIV protease sequence of 5 to 100 bases comprising at least one mutation chosen from 41S, 41T, 41I, 41K, 41G and 70E, may be useful for in vitro diagnosis of viral drug resistance. In particular, an isolated and purified oligonucleotide comprising a HIV protease sequence of 5 to 100 bases comprising at least one mutation chosen from 41T, 41I, 41K, 41G and 70E, may be useful for in vitro diagnosis of viral drug resistance. Suitable oligonucleotides for nucleic acid amplifying technologies contain 5 to 35 nucleic acid bases. Suitably such oligonucleotides contain 15 to 30 nucleic acid bases. An oligonucleotide may contain the mutant base at the 3' end so as to enable the detection of the mutant using PCR. Oligonucleotides may also be used as probes including molecular beacons (Tyagi, Nature Biotechnol 1998, 16(1) 49-53), and TaqMan probes.

A computer system comprising at least one database correlating the presence of at least one mutation in a human immunodeficiency virus protease and fold change in susceptibility of at least one strain of HIV to a protease inhibitor, comprising at least one record corresponding to a correlation between at least one mutation selected from 41S, 41T, 41I, 41K, 41G and 70E, in particular 41T, 41I, 41K, 41G and 70E, and treatment with at least a protease inhibitor can be used for evaluating resistance towards therapy.

A neural network that predicts the development of therapeutic agent resistance or sensitivity against at least one viral strain comprising at least one mutation selected from 41S, 41T, 41I, 41K, 41G and 70E can be used (WO 01/95230). In particular, a neural network that predicts the development of therapeutic agent resistance or sensitivity against at least one viral strain comprising at least one mutation selected from 41T, 41I, 41K, 41G and 70E can be used (WO01/95230).

Genotyping Methodologies

Resistance of HIV to antiretroviral drugs may be determined at the genotypic level by identifying mutations in the HIV-1 genome and by inferring the resistance of HIV-1 to antiretroviral drugs through searching for mutational patterns known to correlate with resistance. Assays for detection of mutations in HIV-1 may be based on polymerase chain reaction (PCR) amplification of viral genomic sequences. These amplified sequences are then analyzed using either hybridization or sequencing techniques. Hybridization-based assays include primer-specific PCR, which makes use of synthetic oligonucleotides designed to allow selective priming of DNA synthesis. See Larder, B. A., et al., AIDS 5, 137-144 (1991); Richnan, D. D., et al., J. Infect. Dis. 164, 1075-1081 (1991); Gingeras, T. R., et al., J. Infect Dis. 164, 1066-1074 (1991). Only when primer sequences match the target sequence (wild-type or mutant) at the 3' end, is amplification of target sequences possible and DNA fragments are produced. Knowledge of the primer sequences allows one to infer the sequence of the viral isolate under investigation, but only for the region covered by the primer sequences. Other hybridization-based assays include differential hybridization (Eastman, P. S., et al., J. Acq. Imm. Def. Syndr. Human Retrovirol. 9, 264-273 (1995); Holodniy, M., et al., J. Virol. 69, 3510-3516 (1995); Eastman, P. S., et al., J. Clin, Micro. 33, 2777-2780 (1995).); Line Probe Assay (LipA® HIV-11 RT, Innogenetics) (Stuyver, L., et al., Antimicrob. Agents Chemotherap. 41, 284-291 (1997)); and biochip technology such as GENECHIP® technology (Affymetrix) (D'Aquila, R. T. Clin. Diagnost. Virol. 3, 299-316 (1995); Fodor, S. P. A. et al., Nature 364, 555-556 (1993); Fodor, S. P. A. Nature 227, 393-395 (1997). The sequence may also be determined using mass spectroscopic technologies. DNA sequencing assays provide information on all nucleotides of the sequenced region Sequencing results may be reported as amino acid changes at positions in the protease gene and the reverse transcriptase gene compared to the wild-type reference sequence. The changes included in the genotyping report may be limited to mutations at positions known to manifest drug resistance-associated polymorphisms. Polymorphisms at positions not associated with drug resistance may be omitted.

Phenotyping Methodologies

Phenotyping assays measure the ability of a replicating virus to grow in the presence of compounds compared to a wild-type reference virus such as e.g. HIV-1LAI, HIV-1/NL4.3, HIV-1/HXB2 or e.g. HIV-2/ROD. Alternatively, phenotyping assays are performed with pseudotyped viruses not able to replicate (WO 02/38792). Consequently, these assays directly measure the degree of viral susceptibility to specific inhibitors. In this case, one measures the effect of all mutational interactions, the effects of genetic changes as yet unknown or not previously identified, the effect of the background genotype, etc., on the phenotype. Some phenotypic assays are discussed below.

Cytopathic Effect Assay (CPE Assay)

Determination of the antiviral activity of a compound was done as described in Pauwels R. et al. (J Virol Methods 1988; 20(4):309-21). Various concentrations of the test compounds were brought into each well of a flat-bottom microtiter plate. Subsequently, HIV and MT4 cells were added to a final concentration of 200-250 50% cell culture infectious doses ($CCID_{50}$)/well and 30,000 cells/well, respectively. After 5 days of incubation (37° C., 5% $CO_2$), the cytopathic effect of the replicating virus was determined by the tetrazolium colorimetric MTT method. The dose protecting 50% of the cells from virus cytopathic effect was defined as the $EC_{50}$, while the dose achieving 90% protection was defined as the $EC_{90}$.

Reporter Gene Assay

The reporter gene assay used MT4-LTR-EGFP cells. Upon infection by HIV-1, the expression of the viral that product increases transcription from the HIV-1 LTR promoter, leading to high-level expression of the reporter gene product. The assay procedure was similar to the CPE assay, except for the end reading of the assay, which was performed on day 3 by measuring the relative fluorescence of treated cultures and comparing this with the relative fluorescence of untreated cultures. The $EC_{50}$ or the $EC_{90}$ of a compound was defined as the concentration that inhibited the relative fluorescence by 50% or 90% respectively.

Antiviral Assay wth PBMC Cultures

The purification and activation of PBMCs as well as the antiviral assays were carried out as described (CDER. Guidance for Industry Points to Consider in the Preclinical Development of Antiviral Drugs. 1990). The assay measured the extent that a drug inhibits HIV p24 antigen production by peripheral blood mononuclear cells (PBMC) cultures acutely infected with a viral strain. The susceptibility determination uses phytohaemaglutinine (PHA)-stimulated PBMCs from normal donors. In the in vitro infection experiments 1000 $CCID_{50}$ per million PHA-stimulated PBMCs was used. Cultures were split ½ every 3 to 4 days and compound was added together with the addition of new medium.

The p24 antigen production was measured using a commercial kit, according to the manufacturer protocol (NEN), at the moment that the p24 production of untreated infected cultures is maximal; i.e. between 7 and 11 days after infection. The % p24 production was calculated by means of following equation:

$$\%p24 = 100 \times \frac{[p24]\text{Sample} - [p24]\text{Mock\_Control}}{[p24]\text{HIV\_Control} - [p24]\text{Mock\_Control}}$$

where $[p24]_{Sample}$ is the p24 concentration in an infected treated culture, $[p24]_{HIV\_Control}$ is the p24 concentration in an infected untreated culture and $[p^{24]}_{Mock\_Control}$ is the p24 concentration in a mock-infected culture. The dose achieving 50% p24 production according to the above formula was defined as the $EC_{50}$, while the dose achieving 10% p24 production according to the above formula was defined as the $EC_{90}$.

Antiviral Assay with monocytes/macrophages The assay measured the extent that a drug inhibits HIV p24 antigen production by primary monocytes/macrophages acutely infected with HIV-1/BaL (300 $CCID_{50}$/ml). The susceptibility determination used monocytes/macrophages isolated from PBMCs from normal donors by plastic adherence. Every 5 days cultures were fed with complete medium containing the appropriate compound concentrations. The p24 antigen production was measured at day 14 after virus challenge and $EC_{50}$ and $EC_{90}$ values were calculated.

Recombinant Virus Assays

A recombinant virus assay (RVA) starts with the amplification of viral target sequences by means of PCR. The amplicons are incorporated into a proviral laboratory clone deleted for the sequences, present in the amplicon. This generates a stock of recombinant viruses. The viruses are tested for their ability to grow in the presence of different concentrations of drugs. Results are obtained by calculating $EC_{50}$ values for each inhibitor and by reporting the results as $EC_{50}$ values, expressed in μM concentrations, or by computing the ratio of the $EC_{50}$ values found for the recombinant virus to the $EC_{50}$ values found for a wild type susceptible laboratory virus tested in parallel. In the latter case, resistance is expressed as "fold-resistance" (fold change in susceptibility, FC) compared to a wild-type susceptible HIV-1 strain.

The use of reporter gene systems for susceptibility testing allows the implementation of laboratory automation and standardization (Pauwels, et al., J. Virol. Methods 20, 309-321 (1988); Paulous, S., et al., International Workshop on HIV Drug Resistance, Treatment Strategies and Eradication, St. Petersburg, Fla., USA. Abstr. 46 (1997); and Deeks, S. G., et al., 2nd International Workshop on HIV Drug Resistance and Treatment Strategies, Lake Maggiore, Italy. Abstr. 53 (1998)).

The Antivirogram® assay (Virco) (WO 97/27480) is based on homologous recombination of patient derived HIV-1 gag/PR/RT sequences into a proviral HIV-1 clone correspondingly deleted for the gag/PR/RT sequences. A similar assay (Phenosense® ViroLogic, WO 97/27319) is based on enzymatic ligation of patient-derived PR/RT sequences into a correspondingly deleted proviral vector carrying an indicator gene, luciferase, inserted in the deleted HIV-1 envelope gene. Another assay was developed by Bioalliance (Phenoscript, WO 02138792). The development of high throughput phenotyping and genotyping assays has allowed the establishment of a database containing the phenotypic resistance data and the genotypic sequences of over 30,000 clinical isolates.

EXPERIMENTAL PART

Example 1

The Identification of Mutational Patterns in HIV-1 Protease and the Correlated Phenotypic Resistance Plasma samples from HIV-1-infected individuals from routine clinical practice were obtained and shipped to the laboratory on dry ice and stored at −70° C. until analysis. Viral RNA was extracted from 200 μL patient plasma using the QIAAMP® Viral RNA Extraction Kit (Qiagen, Hilden, Germany), according to the manufacturers instructions. cDNA encompassing part of the pol gene was produced using Expand™ reverse transcriptase (Boehringer Mannheim). A 2.2 kb fragment encoding the protease and RT regions were amplified from patient-derived viral RNA by nested polymerase chain reaction (PCR) using PCR primers and conditions as described. (Hertogs K., et al., Antimicrob. Agents Chemother. 42: 269-276 (1998), WO 01/81624). This genetic material was used in phenotyping and genotyping experiments.

Phenotypic analysis was performed using the recombinant virus assay (Antivirogram®)(WO 97127480). MT-4 cells (Harada S., et al, Science 229: 563-566 (1985).) were co-transfected with pol gene PCR fragments and the protease-RT deleted HIV-1 molecular clone, pGEM3ΔPRT. This resulted in viable recombinant viruses containing protease/RT from the donor PCR fragment. After homologous recombination of amplicons into a PR-RT deleted proviral clone, the resulting recombinant viruses were harvested, titrated and used for in vitro susceptibility testing to antiretroviral drugs. The results of this analysis were expressed as fold change in susceptibility, reflecting the fold change in mean $EC_{50}$ (μM) of a particular drug when tested with patient-derived recombinant virus isolates, relative to the mean $EC_{50}$ (μM) of the same drug obtained when tested with a reference wild-type virus isolate (IIIB/LAI).

Genotyping was performed by an automated population-based full-sequence analysis, through a dideoxynucleotide-based approach, using the BigDye™ terminator kit (Applied Biosystems, Inc.) and resolved on an ABI 377 DNA sequencer.

The genotypes are reported as amino acid changes at positions along the protease gene compared to the wild-type (HXB2) reference sequence. Analysis by VirtualPhenotype™ interpretational software (WO 01/79540) allowed detection of mutational patterns in the database containing the genetic sequences of the clinical isolates and linkage with the corresponding resistance profiles of the same isolates.

Example 2

Susceptibility Analysis of HIV-1 Variants Constructed by Site-directed Mutagenesis Mutations in the protease or RT coding region were created by site-directed mutagenesis, using the QuikChange® Site-Directed Mutagenesis Kit (STRATAGENE®), of a wild-type HXB2-D EcoRI-PstI restriction enzyme fragment, encompassing the HIV-1 pol gene and cloned into pGEM3 (Promega). All mutant clones were verified by DNA sequence analysis. PCR fragments were prepared from the mutated clones and the altered protease coding regions were transferred into HIV-1 HBXB2-D by homologous recombination as described above. The susceptibility of these recombinant viruses to drugs was determined by the MT-4 cell CPE protection assay.

Example 3

In vitro Selection of Resistant Strains

MT4-LTR-EGFP cells were infected at a multiplicity of infection (MOI) of 0.01 to 0.001 $CCID_{50}$/cell in the presence of inhibitor. The starting concentration of the inhibitor was two to tee times the $EC_{50}$, a suboptimal concentration. The cultures were sub-cultivated and scored microscopically on virus-induced fluorescence and cytopathicity every 3-4 days. The cultures were sub-cultivated in the presence of the same compound concentration until signs of virus replication were observed. The escaping virus was further cultivated in the presence of the same inhibitor concentration in order to enrich the population in resistant variants. If full virus breakthrough was observed the supernatant was collected and stored (new virus strain). Afterwards, the same virus was challenged with a higher compound concentration in order to select variants able to grow in the presence of as high as possible inhibitor concentrations. From the new viruses, a virus stock was grown in the absence of inhibitor.

In vitro drug selection experiments starting from wild-type HIV-1 under pressure of compound 1, compound 2, and Nelfinavir (NFV) have been performed. Tables 1, 2, 3, 4, and 5 show the genotypic and phenotypic characterization of the selected strains.

TABLE 1

Characterization of the strains isolated from HIV-1/LAI in the presence of compound 1

In vitro selection
Experimental conditions

| Starting strain | | HIV/LAI | HIV-1/LAI | HIV-1/LAI | HIV-1/LAI |
|---|---|---|---|---|---|
| Compound Concentration (nM) | | — | Compound 1 30 | Compound 1 100 | Compound 1 100 |
| Days | | — | 45 | 97 | 188 |
| Protease Genotype | | | | | |
| Mutations | | — | R41T | R41T K70E | R41T K70E |
| Phenotype In vitro susceptibility to PIs N, median EC50 (nM), median FC | | | | | |
| Compound 1 | N | 37 | 7 | 6 | 3 |
| | EC50 | 3.2 | 7.7 | 26 | 44 |
| | FC | 1 | 2 | 8 | 10 |
| Indinavir | N | 16 | 3 | 3 | 2 |
| | EC50 | 28 | 33 | 98 | 140 |
| | FC | 1 | 1 | 4 | 5 |
| Ritonavir | N | 16 | 3 | 3 | 2 |
| | EC50 | 31 | 32 | 21 | 46 |
| | FC | 1 | 1 | 1 | 1 |
| Nelfinavir | N | 11 | 3 | 4 | 2 |
| | EC50 | 30 | 32 | 18 | 37 |
| | FC | 1 | 1 | 1 | 1 |
| Saquinavir | N | 46 | 2 | 6 | 3 |
| | EC50 | 7.8 | 30 | 35 | 150 |
| | FC | 1 | 4 | 4 | 20 |
| Amprenavir | N | 67 | 3 | 6 | 3 |
| | EC50 | 36 | 38 | 29 | 39 |
| | FC | 1 | 1 | 1 | 1 |
| Lopinavir | N | 11 | 3 | 5 | 3 |
| | EC50 | 7.9 | 27 | 32 | 47 |
| | FC | 1 | 3 | 4 | 6 |

TABLE 2

Characterization of the strains isolated from HIV-1/LAI in the presence of compound 1

In vitro selection
Experimental conditions

| Starting strain | | HIV-1/LAI | HIV-1/LAI | HIV-1/LAI | HIV-1/LAI | HIV-1/LAI |
|---|---|---|---|---|---|---|
| Compound Concentration (nM) | | — | Comp 1 30 | Comp 1 100 | Comp 1 100 | Comp 1 200 |
| Days | | — | 70 | 139 | 195 | 328 |
| Protease Genotype | | | | | | |
| Mutations | | — | S37S/N R41R/K K70E | S37N R41S K70E | S37N R41S K70E | |
| Phenotype In vitro susceptibility to PIs N, median EC$_{50}$ (nM), median FC | | | | | | |
| Compound 1 | N | 5 | 1 | 1 | 1 | 1 |
| | EC50 | 2.6 | 6.5 | 2.5 | 4.7 | 0.4 |
| | FC | 1 | 3 | 1 | 2 | 0.2 |
| IDV | N | 4 | 1 | 1 | 2 | 1 |
| | EC50 | 12 | 18 | 6.3 | 9.1 | 5.5 |
| | FC | 1 | 2 | 1 | 1 | 0.5 |
| RTV | N | 3 | 1 | 1 | 2 | 1 |
| | EC50 | 33 | 47 | 22 | 14 | 31 |
| | FC | 1 | 1 | 1 | 0.4 | 1 |
| NFV | N | 4 | 1 | 1 | 2 | 1 |
| | EC50 | 38 | 39 | 9.7 | 9.5 | 1.9 |
| | FC | 1 | 1 | 0.3 | 0.3 | 0.1 |
| SQV | N | 3 | 1 | 1 | 1 | 1 |
| | EC50 | 5.6 | 6.0 | 0.7 | 0.9 | 4.0 |
| | FC | 1 | 1 | 0.1 | 0.2 | 1 |
| APV | N | 5 | 1 | 1 | 2 | 1 |
| | EC50 | 20 | 56 | 24 | 14 | 15 |
| | FC | 1 | 3 | 1 | 1 | 1 |
| LPV | N | 5 | 1 | 1 | 2 | 1 |
| | EC50 | 4.6 | 17 | 2.8 | 3.9 | 1.1 |
| | FC | 1 | 4 | 1 | 1 | 0.2 |

TABLE 3

Characterization of the strains isolated from HIV-1/LAI in the presence of compound 2

In vitro selection
Experimental conditions

| Starting strain | | HIV-1/LAI | HIV-1/LAI | HIV-1/LAI | HIV-1/LAI |
|---|---|---|---|---|---|
| Compound Concentration (nM) | | — | Compound 2 100 | Compound 2 100 | Compound 2 100 |
| Days | | — | 116 | 200 | 264 |
| Protease Genotype | | | | | |
| Mutations | | — | R41I | G16G/H R41I | G16E R41I |
| Phenotype In vitro susceptibility to PIs N, median EC$_{50}$ (nM), median FC | | | | | |
| Compound 2 | N | 2 | | 2 | 1 |
| | EC50 | 12 | | 6.9 | 61 |
| | FC | 1 | | 1 | 5 |
| IDV | N | 4 | | 1 | 1 |
| | EC50 | 12 | | 19 | 47 |
| | FC | 1 | | 2 | 4 |
| RTV | N | 3 | | 2 | 1 |
| | EC50 | 33 | | 22 | 23 |
| | FC | 1 | | 1 | 1 |
| NFV | N | 4 | | 2 | 1 |
| | EC50 | 38 | | 16 | 14 |
| | FC | 1 | | 0 | 0 |

TABLE 3-continued

Characterization of the strains isolated from
HIV-1/LAI in the presence of compound 2

| | | | | |
|---|---|---|---|---|
| SQV | N | 3 | | 1 |
| | EC50 | 5.6 | | 45 |
| | FC | 1 | | 8 |
| APV | N | 5 | 2 | 1 |
| | EC50 | 20 | 14 | 8.4 |
| | FC | 1 | 1 | 0 |
| LPV | N | 5 | 2 | 1 |
| | EC50 | 4.6 | <0.9 | 18 |
| | FC | 1 | 0 | 4 |

TABLE 4

Characterization of the strains isolated from
HIV-1/LAI in the presence of compound 1

| In vitro selection Experimental conditions | | | | | |
|---|---|---|---|---|---|
| Starting strain | HIV-1/LAI | HIV-1 | HIV-1 | HIV-1 | HIV-1 |
| Compound | — | — | Comp 1 | Comp 1 | Comp 1 |
| Concentration (nM) | — | — | 20 | 40 | 40 |
| Days | — | — | 94 | 161 | 175 |
| Protease Genotype | | | | | |
| Mutations | — | — | R41G/R V82V/I | R41G V82I | R41G V82I |
| Phenotype In vitro susceptibility to PIs N, median EC$_{50}$ (nM), median FC | | | | | |
| Compound 1 | N | 5 | 1 | 1 | 1 | 1 |
| | EC50 | 2.6 | 3.4 | 1.1 | 2.6 | 1.9 |
| | FC | 1 | 1 | 0 | 1 | 1 |
| IDV | N | 4 | 1 | 1 | 1 | 1 |
| | EC50 | 12 | 2.4 | 3.1 | 2.1 | 3.9 |
| | FC | 1 | 0 | 0 | 0 | 0 |
| RTV | N | 3 | 1 | 1 | 1 | 1 |
| | EC50 | 33 | 22 | 4.2 | 6.3 | 1.7 |
| | FC | 1 | 1 | 0 | 0 | 0 |
| NFV | N | 4 | 1 | 1 | 1 | 1 |
| | EC50 | 38 | 31 | 5.7 | 11 | 16 |
| | FC | 1 | 1 | 0 | 0 | 0 |
| SQV | N | 3 | 1 | 1 | 1 | 1 |
| | EC50 | 5.6 | 8.9 | 0.9 | 1.0 | 0.8 |
| | FC | 1 | 2 | 0 | 0 | 0 |
| APV | N | 5 | 1 | 1 | 1 | 1 |
| | EC50 | 20 | 26 | 7.3 | 6.6 | 9.4 |
| | FC | 1 | 1 | 0 | 0 | 0 |
| LPV | N | 5 | 1 | 1 | 1 | 1 |
| | EC50 | 4.6 | 6.8 | 2.0 | 1.8 | 1.0 |
| | FC | 1 | 1 | 0 | 0 | 0 |

TABLE 5

Characterization of the strains isolated from
HIV-1/LAI in the presence of nelfinavir (NFV)

| In vitro selection Experimental conditions | | | | | |
|---|---|---|---|---|---|
| Starting strain | HIV-1/LAI | HIV-1/LAI | HIV-1/LAI | HIV-1/LAI | HIV-1/LAI |
| Compound | — | NFV | NFV | NFV | NFV |
| Concentration (nM) | — | 1000 | 3000 | 9000 | 9000 |
| Days | — | 35 | 69 | 111 | 140 |
| Protease Genotype | | | | | |
| Mutations | — | D30N | L10F D30N | L10F D30N R41R/K K45I/K | L10F D30N R41R/K K45I/K |

TABLE 5-continued

Characterization of the strains isolated from
HIV-1/LAI in the presence of nelfinavir (NFV)

| | | | | M46I | M46I V77I I85V/I N88D/N | M46I V77I I84V/I I85V/I N88D | M46I V77I I84V N88D |
|---|---|---|---|---|---|---|---|
| Phenotype In vitro susceptibility to PIs N, median EC$_{50}$ (nM), median FC | | | | | | | |
| IDV | N | 4 | 1 | | | 1 | 1 |
| | EC50 | 12 | 7.9 | | | 100 | 28 |
| | FC | 1 | 1 | | | 8 | 2 |
| RTV | N | 3 | 1 | 1 | 1 | 1 | 1 |
| | EC50 | 33 | 19 | 27 | 86 | 170 | |
| | FC | 1 | 1 | 1 | 3 | 5 | |
| NFV | N | 4 | 1 | | | 1 | 1 |
| | EC50 | 38 | 330 | | | 7200 | 6800 |
| | FC | 1 | 9 | | | 200 | 200 |
| SQV | N | 3 | 1 | 1 | | 1 | 1 |
| | EC50 | 5.6 | 1.8 | 2.5 | | 15 | 34 |
| | FC | 1 | 0 | 0 | | 3 | 6 |
| APV | N | 5 | 1 | 1 | 1 | 1 | |
| | EC50 | 20 | 28 | 59 | 95 | 190 | |
| | FC | 1 | 1 | 3 | 5 | 10 | |
| LPV | N | 5 | 1 | 1 | 1 | 1 | |
| | EC50 | 4.6 | 7.7 | 24 | 39 | 56 | |
| | FC | 1 | 2 | 5 | 8 | 10 | |

The in vitro antiviral activity of compound 1, compound 2, Nelfinavir, and current PIs against the selected strains was evaluated in acutely infected MT4 cells. Median EC$_{50}$ values together with the number of determinations (N), and the fold change in EC$_{50}$ as compared to wild type (FC) are reported.

The invention claimed is:

1. A method for identifying a drug effective against mutant HIV protease, comprising:
   (i) providing a nucleic acid comprising mutant HIV protease comprising at least one mutation chosen from R41S, R41T, R41I, R41G and K70E as compared to the wild-type HIV strain IIIB/LAI;
   (ii) recombining said nucleic acid comprising mutant HIV protease of step (i) into a proviral nucleic acid deleted for said nucleic acid to generate a recombinant HIV virus;
   (iii) determining a phenotypic response to said drug for said HIV recombinant virus; and
   (iv) identifying a drug effective against mutant HIV based on the phenotypic response of step (iii).

2. A method for identifying a drug effective against mutant HIV protease, comprising:
   (i) providing a nucleic acid comprising mutant HIV protease comprising at least one mutation chosen from R41T, R41I, R41G and K70E as compared to the wild-type HIV strain IIIB/LAI;
   (ii) recombining said nucleic acid comprising mutant HIV protease of step (i) into a proviral nucleic acid deleted for said nucleic acid to generate a recombinant HIV virus;

(iii) determining a phenotypic response to said drug for said HIV recombinant virus;
(iv) identifying a drug effective against mutant HIV based on the phenotypic response of step (iii).

3. A method for identifying a drug effective against mutant HIV protease, comprising:
   (i) providing a HIV protease comprising at least one mutation chosen from R41S, R41T, R41I, R41G and K70E as compared to the wild-type HIV strain IIIB/LAI;
   (ii) determining the activity of said drug on said HIV protease;
   (iii) determining the activity of said drug on wild type HIV protease;
   (iv) determining the ratio of the activity determined in step (iii) over the activity determined in step (ii); and
   (v) identifying an effective drug against mutant HIV based on the ratio of step (iv).

4. A method for identifying a drug effective against mutant HIV protease, comprising:
   (i) providing a HIV protease comprising at least one mutation chosen from R41T, R41I, R41G and K70E as compared to the wild-type HIV strain IIIB/LAI;
   (ii) determining the activity of said drug on said HIV protease;
   (iii) determining the activity of said drug on wild type HIV protease;
   (iv) determining the ratio of the activity determined in step (iii) over the activity determined in step (ii); and
   (v) identifying an effective drug against mutant HIV based on the ratio of step (iv).

5. A method for identifying a change in drug effectiveness against mutant HIV protease, comprising:
   (i) providing a HIV protease comprising at least one mutation chosen from R41S, R41T, R41I, R41G and K70E as compared to the wild-type HIV strain IIIB/LAI;
   (ii) determining the activity of said drug towards said HIV protease;
   (iii) determining the activity of said drug on wild type HIV protease;
   (iv) determining the ratio of the activity determined in step (iii) over the activity determined in step (ii); and
   (v) identifying a change in drug effectiveness against mutant HIV based on the ratio of step (iv).

* * * * *